US012644613B2

(12) United States Patent
Dechert et al.

(10) Patent No.: US 12,644,613 B2
(45) Date of Patent: Jun. 2, 2026

(54) DEVICE AND METHOD FOR CARRYING OUT DECONTAMINATION MEASURES, METHOD FOR PREPARING DECONTAMINATION MEASURES AND METHOD FOR MONITORING DECONTAMINATION MEASURES

(71) Applicants: Michael Dieter Dechert, Ober-Ramstadt (DE); Silvano Georg, Weiterstadt (DE)

(72) Inventors: Michael Dieter Dechert, Ober-Ramstadt (DE); Silvano Georg, Weiterstadt (DE)

( * ) Notice: Subject to any disclaimer, the term of this patent is extended or adjusted under 35 U.S.C. 154(b) by 675 days.

(21) Appl. No.: 17/925,176

(22) PCT Filed: May 14, 2021

(86) PCT No.: PCT/EP2021/062872
    § 371 (c)(1),
    (2) Date: Nov. 14, 2022

(87) PCT Pub. No.: WO2021/229074
    PCT Pub. Date: Nov. 18, 2021

(65) Prior Publication Data
    US 2023/0175714 A1     Jun. 8, 2023

(30) Foreign Application Priority Data

May 15, 2020   (WO) ................. PCT/EP2020/063710
Jun. 5, 2020   (WO) ................. PCT/EP2020/065694
Mar. 16, 2021  (DE) .................... 10 2021 106 401.5

(51) Int. Cl.
    *F24F 3/163*     (2021.01)
    *A61L 2/22*      (2006.01)
    (Continued)

(52) U.S. Cl.
    CPC ................ *F24F 3/163* (2021.01); *A61L 2/22* (2013.01); *B08B 15/02* (2013.01); *F24F 7/08* (2013.01);
    (Continued)

(58) Field of Classification Search
    CPC .... F24F 3/163; F24F 11/74; F24F 7/08; F24F 9/00; F24F 2120/10; F24F 2110/50;
    (Continued)

(56) References Cited

U.S. PATENT DOCUMENTS 5,350,337 A * 9/1994 Kondo ...................... F24F 9/00
                                                        454/189
6,217,437 B1 * 4/2001 Murray .................. A01K 1/031
                                                        119/500

(Continued)

FOREIGN PATENT DOCUMENTS

CN        109059050 A     12/2018
EP        1054219 A1      11/2000
          (Continued)

*Primary Examiner* — Steven B McAllister
*Assistant Examiner* — Dana K Tighe

(57) ABSTRACT

A method for preparing decontamination measures within a room located in a building and used by people includes a planning acquisition step. Therein, a plurality of regions of use within the room are identified, and for each region an expected use intensity is determined based on previously determined parameters. In a subsequent planning implementation step, for each region of use, proceeding from the expected use intensity, a suction means assigned to said region of use and having an associated supply air volume flow is specified. In a method by carrying out the decontamination measures, while the decontamination measures are being carried out, operation of individual suction means is adjusted to an actual use of the assigned region of use by people, and a suction volume flow suctioned by the suction (Continued)

means in question is specified, between a minimum value specified for the suction means in question, and a maximum value.

9 Claims, 7 Drawing Sheets

(51) Int. Cl.

| | |
|---|---|
| *B08B 15/02* | (2006.01) |
| *F24F 7/08* | (2006.01) |
| *F24F 9/00* | (2006.01) |
| *F24F 11/74* | (2018.01) |
| *A61L 103/75* | (2026.01) |
| *F24F 110/50* | (2018.01) |
| *F24F 120/10* | (2018.01) |

(52) U.S. Cl.
CPC ................ *F24F 9/00* (2013.01); *F24F 11/74* (2018.01); *A61L 2103/75* (2026.01); *F24F 2009/002* (2013.01); *F24F 2110/50* (2018.01); *F24F 2120/10* (2018.01)

(58) Field of Classification Search
CPC .. F24F 2009/002; A61L 2/22; A61L 2202/25; B08B 15/02
USPC .......................................................... 454/191
See application file for complete search history.

(56) References Cited

U.S. PATENT DOCUMENTS

| | | | | |
|---|---|---|---|---|
| 9,050,382 | B2 * | 6/2015 | Carr .......................... A61L 9/02 |
| 11,207,630 | B2 * | 12/2021 | Sahiholnasab ....... B01D 46/444 |
| 2006/0154590 | A1 | 7/2006 | Kanaya |
| 2021/0003301 | A1 | 1/2021 | Takayanagi |
| 2021/0025607 | A1 * | 1/2021 | Torres .................... B08B 15/02 |
| 2021/0033294 | A1 * | 2/2021 | Grabon ................. A45B 23/00 |

FOREIGN PATENT DOCUMENTS

| | | |
|---|---|---|
| EP | 1134509 A1 | 9/2001 |
| GB | 2180054 A | 3/1987 |
| WO | 2013021466 A1 | 2/2013 |
| WO | 2020003867 A1 | 1/2020 |

* cited by examiner

DEVICE AND METHOD FOR CARRYING OUT DECONTAMINATION MEASURES, METHOD FOR PREPARING DECONTAMINATION MEASURES AND METHOD FOR MONITORING DECONTAMINATION MEASURES

TECHNICAL FIELD

The disclosure relates to a method for preparing decontamination measures within a room located in a building and used by people. The disclosure furthermore relates to a method for carrying out decontamination measures in the room located in a building and used by people, wherein the method for preparing decontamination measures was carried out previously. The disclosure furthermore relates to a method for monitoring the decontamination measures carried out by the disclosed method.

BACKGROUND

Decontamination measures are known from practice, by means of which for example an object soiled by contamination harmful to the environment or to people can be decontaminated. The contamination to be removed can for example be radioactive, biological or chemical impurities. The objects in question can be brought into a cleaning room provided for this purpose, and be cleaned and decontaminated there. It is also known from practice that, by means of transportable cleaning devices, decontamination of objects or people can take place at a location at which contamination occurs or at which decontamination is to be occasionally carried out.

In various fields, such as in pharmaceutics or in semiconductor manufacture, industrial method steps, in which as pure an environment as possible is required, are carried out in cleanrooms specifically provided for this. Impurities often undesired relates to suspended particles in the air, which, depending on the size of the suspended particles, remain suspended in the air for a long period of time, and can deposit and collect on all accessible surfaces. In these cleanrooms, a volume of air located therein is typically suctioned continuously and replaced by filtered and cleaned supply air. In this way, impurities found in the room air can be discharged from the cleanroom and the cleanroom can be decontaminated as a result. In order to prevent contamination by people or by objects carried by the people, airlock systems are often required. Furthermore, it can be provided for a person to wear separate cleanroom clothing while in the cleanroom, which clothing is cleaned and does not comprise any contaminating impurities.

Depending on the intensity of the decontamination measures carried out, such as the circulation of the air volume in the cleanroom and the filtering of the supply air, a different cleanroom quality can be achieved. Standardized cleanroom classes are known, wherein the classification of the air purity is divided according to the particle concentrations for individual particle size ranges.

Since in many cases, contamination of a cleanroom occurs in particular due to people entering the room and staying in the room, many cleanrooms are designed such that the number of people spending time therein is kept as low as possible, and in particular the frequency with which individual people enter or leave the cleanroom is minimized as far as possible.

SUMMARY

Decontamination measures developed and correspondingly designed for cleanrooms are not readily suitable for rooms having a changing occupancy of people. Nonetheless, it may be advantageous to carry out decontamination measures continuously, in a room within a building that is used by a plurality of or many people, in order to keep the risk of contamination of individual people, located in the room, as low as possible.

The object of the present disclosure is therefore considered that of designing a method for preparing decontamination measures such that, depending on the desired result of the decontamination measures, it is possible to carry out the decontamination measures as efficiently as possible with the smallest possible outlay, and such that carrying out the decontamination measures leads to the least possible harm for the people located in the room.

This object is achieved in that, in a planning acquisition step, on the basis of a specified use concept, a plurality of regions of use within the room is identified, and for each region of use an expected use intensity is determined on the basis of previously determined parameters, and wherein, in a subsequent planning implementation step, for each region of use, proceeding from the expected use intensity, a suction means that is assigned to said region of use and has an associated suction volume flow is specified. An essential aspect of the method is the division of the room into different regions of use, in a manner individually adapted to a use concept of the room. The correspondingly divided room then comprises a plurality of regions of use, as well as one or optionally more non-use regions which are separated from one another. In the case of use of the room as intended, for each region of use, a likely use intensity by people present in the region of use in question is determined. In this case, the individual people are considered a potential cause of contamination of the room, with the result that a higher risk of contamination is assumed in regions of use having a high use intensity. In this case, the contamination can occur for example by impurities brought in from outside the room. It is also possible that the individual people bring with them or carry in them pathogens such as bacteria or viruses, which can be released during the person's stay in the region of use in question. In this case, there is a particularly high risk of contamination in the case of people who are infected by a viral disease, and constantly release viruses into the ambient air while breathing. The likelihood and intensity with which a person releases particular impurities into the air can be estimated by preceding estimation methods and tests, on the basis of previously ascertained parameters. Individual parameters can for example be the breath volume breathed out by individual people during different activities, or the floating properties and the dwell time of suspended particles, which are considered undesired contamination and should be reduced by the decontamination measures.

On the basis of such information, the associated use intensity can be ascertained for each region of use, on the basis of which information the decontamination measures then required can be determined and specified. The decontamination measures include in particular the suctioning of air out of the region of use, in order to suction the suspended particles contained in the air, for example dust or viruses, out of the region of use, before contamination can take place of other people who are also in the same region of use or at another position within the room. In the planning implementation step, for each suction means the relevant parameters, such as the cross-sectional area of a suction opening, the spacing and the orientation of the suction opening relative to the people during of use as intended of the relevant region of use, and the maximum suction capacity or the maximum suction volume flow achievable by the suction means, can be determined and specified.

It has been found to be advantageous for each region of use to be assigned a separate suction means, and for a suction volume flow to be specified for the suction means in question, with which suction volume flow a sufficiently high suction capacity can be achieved, in order to be able to suction the impurities, released by a person into the air, sufficiently quickly and efficiently, and thereby prevent contamination of other people in the same room.

Studies have shown that, when breathing out, a person breathes out an airstream at an average speed of from approximately 0.3 m/s to 0.5 m/s, wherein a breath volume of on average 8 liters per minute is breathed out in the case of approximately 12 to 15 breaths per minute. In contrast, when speaking, an airstream having an average speed of from approximately 0.5 m/s to 1.25 m/s is breathed out. Each airstream contains a droplet cloud comprising a large number of aerosols of a very wide range of different sizes. In this case, the size of the aerosol particles can extend from invisible droplets having a diameter of less than 10 µm, to clearly visible droplets having a diameter of more than 50 µm. While the larger droplets quickly sink downwards out of the airstream that is breathed out, and condense on surfaces located there, in particular small droplets remain in the breathed-out airstream for a long time, and can spread out in the surroundings as suspended particles. On the basis of such information, proceeding from the assigned use intensity it is possible to ascertain, for each region of use, the suction capacity required for suctioning the aerosols breathed out by the people into the region of use as comprehensively as possible, and thereby to prevent breathed-out aerosols being able to spread into adjacent regions of use.

It is also possible for a single suction means to be assigned to a plurality of regions of use within the room. In this case, it is not considered necessary, but advantageous, for the suction means to comprise at least one suction opening for each region of use, through which suction opening a portion of the suction volume flow generated by the suction means can be suctioned. The assignment of a single suction means to a plurality of regions of use is advantageous in particular if these are regions of use having a comparable use intensity.

In the planning implementation step, a targeted airflow can be specified for each individual suction means. A targeted airflow contains in particular the suction region, which is captured by the suction means and from which the suction volume flow is suctioned. Specifications relating to the dimensions of a suction opening of the suction means and to the arrangement and orientation of the suction opening relative to the associated region of use can make it possible, for example, for the air suctioned out of the region of use by the suction means to be suctioned largely or almost exclusively from a smaller region of risk within the larger region of use, wherein the region of risk is the portion of the region of use in which the persons' heads are located during use as intended. A standard suction capacity can thus be specified in such a way that, during operation of the suction means at the specified standard suction capacity, the suctioned air is suctioned largely or exclusively in a specified environment around the suction opening, and simultaneously undesired turbulence within the region of use, or compensating flows from outside the region of use which can be felt by people, are reduced or prevented.

Optionally, supplementary structural measures can also be specified in the planning implementation step, in order, for example, to bring about a targeted airflow or an airstream progression specified or supported by said structural measures, within the region of use, for example by partitions or by surfaces, arranged in a suitable manner, within or in the immediate vicinity of the region of use.

A non-use region in a room differs from a region of use in the room in that it is assumed that people stay only comparatively rarely in the non-use region, such that no separate suctioning of room air from the non-use region is required. The suctioning of air from the regions of use forces an air circulation within the room, such that air also flows out of the non-use region into a region of use, and is suctioned there.

However, in addition to the suctioning of air from the regions of use, it may also be expedient for a suction means to additionally be provided at a suitable location within the room, which suction means, in addition to the individual suction means in the regions of use, suctions room air out of the non-use region. In this case, however, it is provided for the suctioning of room air out of the non-use region to be operated at a lower suction capacity or a lower suction volume flow than in the case of the suctioning out of the regions of use, in order not to impair the targeted suctioning of air out of the regions of use. Instead of an additional suction means, it can also be provided for all the individual suction means, which are assigned to the regions of use, to be operated at a slightly higher suction capacity, in order to reduce an exchange duration for a complete exchange of the room air, also out of the non-use regions in the room. It has been found that an exchange of the room air 30 times per hour significantly reduces the risk of contamination for the people in the room.

According to an advantageous embodiment of the inventive concept it is provided that, in the planning implementation step, for each region of use, proceeding from the expected use intensity, an air supply means assigned to said region of use and having an associated supply air volume flow is specified. The amount of air suctioned out by the suction means has to be returned to the region of use, in order to prevent an excessive negative pressure in the region of use, which could impair the use of the region of use as intended, by people. In order to reduce the risk of contamination of an individual region of use by an uncontrolled inflow of air from the surroundings, the use of an air supply means assigned to the relevant region of use is considered advantageous. Depending on the expected use intensity, a supply air volume flow that is adjusted to the air supply means can be specified for said air supply means.

Fresh air is supplied to the room, by a suitable air supply means, as compensation for the room air suctioned out by the individual suction means. In this case, unpolluted air from the surroundings, for example from outside a building, can be supplied as fresh air. It is also possible for the room air suctioned out to be cleaned and processed by suitable processing means, such as filter means or treatment with UV light, or by dielectric barrier discharge, in order to subsequently be supplied to the room again as fresh air. Both a single air supply means, which supplies fresh air to the room at a suitable location, and the air supply means optionally assigned to the individual regions of use are connected to a fresh air reservoir or to a plurality of fresh air reservoirs, wherein the fresh air is previously filtered and cleaned before being supplied to the room. For this purpose, for example transportable or permanently installed filter means can be specified. For many application cases particulate filters are suitable, which meet the requirements of the filter classes H13 or H14 according to the standard EN 1822-1: 2009, and are referred to as HEPA filters.

The individual adjustment of the suction means and the air supply means to individual regions of use and the use intensity expected for the relevant regions of use makes it possible, in principle, to plan and provide different suction means or air supply means which are as efficient as possible can be used cost-effectively for each region of use. In this manner, a concept of decontamination measures planned in this way can be implemented, and carried out during use of the room by people, with the least possible outlay and at low cost.

Suitable specification of the air supply means furthermore makes it possible for a targeted airflow within a region of use to be assisted. It could thus be specified, for example, that an injection opening of the air supply means is adjusted for the relevant region of use, with regard to its dimensions and arrangement on the suction opening of the suction means, and that the injection opening is arranged opposite the suction opening, such that substantially the quantity of air supplied by the air supply means is suctioned by the suction means. Optionally, in this case, a substantially laminar flow from the injection opening to the suction opening can be provided. Expediently, the suction capacity of the suction means and the delivery rate of the air supply means are then matched to one another, such that no pressure difference can build up during operation.

It can also be provided for an air curtain, surrounding the region of use along a peripheral edge of the region of use, to be created by a suitable arrangement and design of the suction means and the air supply means, by means of which air curtain an exchange of quantities of air between the region of use and the surroundings is reduced or largely prevented. Depending on a room use concept and the individual regions of use, as well as the use intensity assigned in each case, it may also be expedient to shield a region of use from the surroundings, using an air curtain of this kind, merely along a portion of the peripheral edge of the region of use, in order, for example, to separate two adjacent regions of use, having a high use intensity, from one another, while an air curtain towards adjacent regions without high use intensity is not required.

According to a particularly advantageous embodiment of the inventive concept, it is provided that, for each region of use, a suction flow is specified, at a specifiable breathable air altitude, by the suction means assigned to said region of use and optionally by the air supply means assigned to said region of use, which suction flow conveys air from the breathable air altitude to the suction means. The altitude within the region of use in which the people using the region of use, in which the people using the region of use breath out the largest breathable air volume during use as intended of the region of use, can be specified as the breathable air altitude. In order to prevent the aerosols contained in a breathed out air volume from being able to be distributed unimpeded in the surroundings, the arrangement and the operating properties of the suction means and optionally the air supply means can generate a suction flow in the region of use which is sufficient for capturing aerosols breathed out in the breathable air altitude, up to a specifiable size, and carry these along with the suction flow. Studies have shown that, in many application cases, the suction flow can be specified such that aerosols up to a diameter of approximately 50 µm can be captured by the suction flow and conveyed to the suction means, without the suction flow being perceived, by people within the region of use, as an unacceptable nuisance during a stay in the region of use.

Particularly advantageously it can furthermore be provided that, for each region of use, the suction flow forms an air curtain, directed towards the suction means, via the suction means assigned to said region of use and optionally via the air supply means assigned to said region of use, by means of which air curtain at least two use cells within the region of use are specified, between which cells an air exchange is prevented, at least at the specifiable breathable air altitude. The air curtain forms a vertical air curtain which reduces or can completely prevent an exchange of air between opposite sides of the air curtain. In this case, depending on the arrangement and orientation of the suction means and the air supply means, the suction flow can flow from bottom to top or from top to bottom, in the region of use.

In all application cases it can be provided for furniture to be arranged within the region of use, and for people to spend time on said furniture, during use as intended of the region of use. An example for this is a dining table in a restaurant, at which one or more people, in each case, can be served on opposite sides. The air supply means can then comprise for example a strip-shaped outlet opening which is arranged on the dining table and is open at the top, and the suction means can be arranged over the outlet opening, above the breathable air altitude, such that a strip-shaped vertical air curtain from the outlet opening towards the suction means is created. The strip-shaped outlet opening can for example extend along the center of the dining table, and separate use cells with in the region of use, located on both sides of the dining table, from one another by means of the air curtain, such that the breathable air breathed out by a person on a first side of the dining table cannot reach a person on the opposite side of the dining table. It is also possible for each individual seat at the dining table to be surrounded by an air curtain and thus isolated from adjacent or opposite seats.

It can be provided for a negative pressure to be generated in the room, while the decontamination measures are being carried out. The specifications for the individual suction means having the suction volume flow, assigned in each case, for the individual regions of use and for air supply means, which may additionally be provided, having a supply air volume flow associated in each case, can take into account a negative pressure prevailing in the room, such that different specifications from those in the case of a room without a negative pressure are determined and specified.

It can also be expedient that no negative pressure is generated in the room while the decontamination measures are being carried out, but rather that the suction volume flow suctioned out by a suction means is cleaned and supplied to the room again as a fresh airstream, or is replaced by a fresh airstream suctioned from outside of the room or the building, such that no pressure difference between the room and surrounding regions within or outside of the building is generated.

According to an optional embodiment of the inventive concept, it is provided that, in the planning implementation step, proceeding from the expected use intensity of all the regions of use within the room, disinfection measures to be carried out at temporal intervals are specified, which are performed by a disinfection means in the room. It can thus be specified, for example, that the room should be disinfected by a cold atomization device at regular intervals during a period of non-use by people, for example over night. It can likewise additionally or alternatively be specified that individual or all the surfaces in the room are decontaminated at regular intervals, in that for example the surfaces are wiped or sprayed with a decontamination agent.

By means of the method, for example suitable decontamination measures can be prepared, which can be implemented in a restaurant or at a workstation, in order to reduce the risk of contamination of people spending time in the same room. In this case, it can also be specified for comparatively intensive decontamination measures to be carried out in time periods in which a significant contamination risk by many people is expected, in order for the decontamination measures to be carried out only at a low intensity, or be temporarily suspended, during other times having a low contamination risk.

The invention also relates to a device for carrying out decontamination measures within a room located in a building and used by people, wherein the device comprises, for a region of use having at least two use cells within the region of use, a suction means that is assigned to said region of use, and an air supply means, wherein the suction means comprises a suction opening which is arranged in a flow guidance plate which surrounds the suction opening and is arranged above a specifiable breathable air altitude. For example cubicles are known from practice, in which a region of use is surrounded by curtains or partitions, and air is suctioned out of said cubicle using a suction means. The suction means can be designed in the manner of a common household extractor hood, which conventionally comprises a flat or concavely curved collector plate. A suction opening is often arranged in the middle of the collector plate or along a peripheral edge of the collector plate. A suction means of this kind could also be operated within a larger room, in order to suction the room air located in a capture region of the suction means from said region, and to supply said air to a filter or decontamination means.

However, suction means of this kind are not designed for efficiently preventing contamination of individual use cells from adjacent use cells, within a region of use. Thus, for example, in office spaces having a plurality of users, often movable partitions are erected between individual tables or use cells, or transparent separating panes are erected between two office table regions, in order to bring about separation of the relevant regions of the various use cells.

An object of the present invention is therefore considered to be that of designing a device for carrying out decontamination measures in such a way that different use cells within a region of use can be isolated from one another as effectively as possible, and the spread of pathogens over a plurality of use cells is prevented.

This object is achieved by a device which additionally comprises an air supply means having a strip-shaped air supply nozzle which is arranged between two use cells and under the suction opening, which nozzle generates a strip-shaped supply airstream such that, when the device is operated as intended, an initially strip-shaped supply airstream from the air supply nozzle is converted into a suction flow which conveys air out of the breathable air altitude to the suction means and suctions it through the suction opening. The strip-shaped air supply nozzle generates a strip-shaped supply airstream which is laminar over a large distance, which airstream is arranged and oriented such that two adjacent use cells are separated from one another by said strip-shaped supply airstream and divided into two room air regions, between which no significant air exchange can take place over the strip-shaped supply airstream. The strip-shaped supply airstream is expediently oriented in such a way, and is blown out of the air supply nozzle at a sufficiently high flow speed, that the supply airstream substantially entirely reaches the capture region of the suction means and is captured by the suction means and suctioned through the suction opening without significant turbulence. The arrangement of the air supply nozzle under the suction means, and in particular directly under the suction opening of the suction means, allows for a very efficient separation of use cells within a region of use, and a correspondingly effective decontamination of the individual use cells.

The suction opening can have a shaping or cross-sectional area which is adapted to the air supply nozzle and is for example also strip-shaped. It is also conceivable, and, according to initial findings, advantageous, for the suction opening to have a round or oval cross-sectional area having a diameter of between 10 cm and 30 cm, preferably between 15 cm and 18 cm. A round suction opening makes it possible for the room air to be captured and suctioned equally well from different directions.

It has been found that an air supply nozzle width of between 0.2 cm and 0.7 cm, and an air supply flow speed of between 1.5 m/s and 2.9 m/s generates a strip-shaped supply airstream which extends initially with a largely laminar flow up to or at least close to the suction means, if said suction means is located between 60 cm and 120 cm, and preferably approximately 80 cm to 100 cm, above the air supply nozzle. Particularly advantageous properties of the supply airstream could be identified in studies for an air supply nozzle width of between 0.4 cm and 0.6 cm, and for an air supply flow speed of between 1.9 m/s and 2.4 m/s. An arrangement of this kind can be implemented for example by a suction means arranged approximately 90 cm above a tabletop, and an air supply nozzle located in the tabletop. It has furthermore been shown that, in the case of a round cross-sectional area of the suction opening having a diameter of 16 cm, a suction speed of approximately 4.5 m/s is sufficient in order to suction, using the suction means, more than 98% of all aerosols and suspended particles which are released in the region between the tabletop and the suction means arranged there above, on one of the two sides of the strip-shaped air supply nozzle.

Studies have shown that a person, when breathing or speaking, breathes out the previously breathed-in air again at a speed in the range between 0.3 m/s and 0.9 m/s. In contrast, the supply airstream supplied via the air supply nozzle, and in particular the exhaust air flow suctioned out using the suction means flows at a significantly higher speed in comparison therewith, such that the quantities of air breathed out during breathing or speaking cannot enter an adjacent use cell via the strip-shaped supply airstream.

Using a device that is designed according to the present disclosure and suitably dimensioned and operated, for example two people can spend time at a shared table top, on opposite sides or use cells, wherein contamination of the opposite use cell in each case can be prevented by the device, without additional partitions or barriers having to be erected between the opposite use cells. In this case, the dimensions of the flow guidance plate can be smaller than the dimensions of the tabletop above which the flow guidance plate of the suction means is arranged. As a result, people can sit at the table and stand up from a sitting position without risking hitting their head on the flow guidance plate.

According to an advantageous embodiment of the inventive concept, it is provided for the flow guidance plate to comprise a convex or planar flow guidance surface facing the air supply means. It has been found that a convex flow guidance surface of the flow guidance plate makes it possible for a flow guide to be crated in the vicinity of the suction opening, by which an effective suctioning of the room air out of the adjacent use cells is promoted.

According to a particularly advantageous embodiment of the inventive concept, it is provided for the flow guidance plate to comprise a suction gap, at least in portions, along the peripheral edge thereof, on the side thereof facing the air supply means, by which gap a Coanda effect, guiding the exhaust air flow along on the flow guidance surface, is generated for an exhaust air flow flowing along a flow guidance surface of the flow guidance plate in the direction of the suction opening. It has been found that a suction gap of this kind along a peripheral edge of the flow guidance plate promotes a particularly long exhaust air flow flowing in a laminar manner along the flow guidance surface, and as a result a particularly large capture region and very efficient capture of the room air in the vicinity of the flow guidance plate can be promoted, without the production of a flow guidance plate of this kind becoming more complex as a result. In this way, turbulence of the suction flow and, associated therewith, an undesired noise development by the suction means can also be reduced.

In order to prevent an excessive portion of the room air being suctioned out of a room during long-lasting or power-intensive operation of the suction means, it may be expedient for the device to comprise at least one diffuser tube which comprises a number of diffuser openings that are spaced apart in the axial direction and are oriented differently in the peripheral directions, through which openings fresh air can be supplied to the region of use. The diffuser tube can for example have a circular cross-sectional area having a diameter of between 10 cm and 25 cm, preferably between 10 cm and 16 cm. Outlet speeds of between 0.15 m/s and 0.4 m/s for the fresh air flowing out of the diffuser tube through the diffuser openings are considered particularly advantageous. Depending on the respective room size and the arrangement of the diffuser tube within the room, a single diffuser tube in the room may be sufficient, or a plurality of diffuser tubes may be arranged within the room.

The diffuser tube can also have a rectangular or triangular cross-sectional area. It is advantageously provided for the diffuser tube to comprise a perforated metal plate-like lateral surface having a plurality of openings, through which fresh air can flow into the region of use. A quantity of fresh air blown into the region of use through the diffuser tube is expediently adjusted to the quantity of room air suctioned by the suction means, such that no pressure drop, unpleasant for people, in the direction of the suction opening results.

It is preferably provided for the diffuser tube to be arranged at a distance from the air supply means and the suction means, along a room edge of the room. The diffuser tube can be laid for example along a room edge formed between the floor and a room wall. As a result, an airstream rising up along the room wall and an airstream extending along the floor can be generated. Studies have shown that, in this way, favorable flow ratios can be specified within the room, in particular for use cells at tables, which flow ratios reduce undesired turbulence and an undesired spread, promoted thereby, of breathable air within the use cells.

It can furthermore be provided, according to an embodiment of the inventive concept, for at least one diffuser tube to be arranged laterally beside the flow guidance plate or above the flow guidance plate. Depending on the respective room size and the size of the use cells, which are allocated a flow guidance plate, it may be advantageous for one diffuser tube or a plurality of diffuser tubes to be arranged either in the immediate vicinity of the flow guidance plate or above the flow guidance plate.

It can also be provided to allow the room air, suctioned by the suction means, to flow through a filter means or through an air treatment system, and, in circulating operation, to feed the filtered or treated quantity of air back to the region of use, through the air supply nozzle and optionally the diffuser tube. An air exchange rate of more than 5/h, and possibly of approximately 7/h and more, can be achieved by means of suitable dimensioning and specification of the parameters relevant for the flow. A suitable specification of the relevant arrangement and dimensions of the air supply nozzle, the suction opening of the suction means, and the diffuser openings of the diffuser tube makes it possible to achieve a particularly quiet operation of the device, which is perceived as comfortable. The noise development during operation can be significantly less than 50 decibels, and optionally less than 45 decibels, such that the operation of the device does not appear disagreeable, even in the case of quiet use of the room as an office.

In order to additionally reduce undesired contamination of the room air with virus-containing aerosols, it can optionally be provided for the device to comprise a room air suction means which comprises room air suction openings above the flow guidance plate. An additional room air suction means makes it possible for a larger air quantity of room air to be suctioned out of the room, without an airstream having a high flow speed, possibly considered unpleasant, being generated. Furthermore, the room air suction means can capture and suction aerosols which do not stay under the flow guidance plate to be suctioned, there, into the flow guidance plate via the suction opening, but rather which enter the surrounding room, laterally past the flow guidance plate, and then can preferably collect and remain above the flow guidance plate.

The room air suction means is expediently arranged annularly around the suction opening, such that in particular quantities of air which are initially in the vicinity of the suction opening, but are not suctioned directly by the suction opening, can be reliably captured and suctioned by the room air suction means. Since the suction opening is advantageously arranged in the immediate vicinity of one or more use cells within a room, in which cells there is an increased risk of contaminated breathable air, a quantity of air associated with risk can be suctioned, in a targeted manner, through an additional room air suction means that surrounds the suction opening.

The room air suction means optionally comprises a room air suction channel which comprises a number of room air suction openings and which annularly surrounds the suction opening, at a distance from the suction opening. The room air suction channel can for example be arranged and fixed on a room ceiling. It is also conceivable for the room air suction channel to be suspended from the room ceiling and to be arranged and extend at a spacing from the room ceiling. The plurality of room air suction openings is in each case designed, dimensioned and oriented such that an advantageous circulating airstream is formed within the room, which airstream is as uniform and consistent as possible, in order to reduce undesired turbulence of the room air.

The room air suction means can also comprise at least one room air suction opening in a suction channel that leads into the suction opening. In this case, no additional room air suction channel is required. Furthermore, aerosols, which rise into higher regions of the room, past the flow guidance plate, can be captured and suctioned through the suction channel above the flow guidance plate.

The invention also relates to a method for carrying out decontamination measures in the room located in a building and used by people, wherein the method described above for preparing said decontamination measures was carried out for the decontamination measures. According to the invention it is provided that, while the decontamination measures are being carried out, operation of individual suction means can be adjusted to an actual use of the assigned region of use by people, and a suction volume flow suctioned by the suction means in question is specified, between a minimum value specified for the suction means in question, and a maximum value. In many cases a suction volume flow reduced to zero, or the deactivation of the relevant suction means, can be specified as the minimum value. The maximum value specified for a suction means can either correspond to a maximally possible operating performance of the suction means, or can be adjusted and specified during the preparation of the decontamination measures, depending on the expected use intensity of the region of use.

While the decontamination measures are being carried out, the operation of individual suction means is expediently adjusted to the actual use of the associated region of use, and as a result it is possible for the decontamination measures to be carried out particularly efficiently. If no, or only a few, people are in the region of use, the suction capacity of the suction means assigned to said region of use can be reduced. In the case of a higher use intensity in comparison thereto, the operation of the assigned suction means can be adjusted and intensified. Since the decontamination measures carried out in the individual regions of use can be individually adjusted to the actual use or to the stay and the activity of people within the region of use, only the decontamination measures actually required are carried out, or the required decontamination measures are carried out only at the required intensity. As a result, significant operating costs can be saved when carrying out the decontamination measures. Furthermore, the nuisance to individual people on account of the decontamination measures carried out in the room can be reduced, and as a result the acceptance of the decontamination measures, by people, can be increased.

The adjustment of the operation of individual suction means to the actual use of the region of use assigned in each case can take place manually. Thus, for example, the currently desired suction capacity or the suction volume flow suctioned by the suction means can be individually specified for each suction means, using a suitable controller.

According to a particularly advantageous embodiment of the inventive concept, it is possible and provided for an actual use of a region of use to be monitored using a sensor means assigned to said region of use, and for the operation of the assigned suction means to be adjusted proceeding from the sensor signals of the sensor means. The sensor means can for example comprise a decibel measuring device and/or a movement sensor, by means of which a sound level prevailing in the region of use, or a movement of people in the region of use, is acquired. It has been found that, for many fields of application, the sound level prevailing in a region of use constitutes a suitable parameter for an actual use of said region of use. The more intensively and louder individual conversations within a region of use are carried out, the higher the risk of contamination, such as viruses, being released into the ambient air in the process. The presence of people in a region of use can be monitored using a movement sensor. The operation of the suction means assigned to said region of use can then be controlled on the basis of the sensor signals of the decibel measuring device or of the movement sensor, such that an automatic adjustment to changing use conditions within the individual regions of use is possible. If the decontamination measures are carried out for example in a restaurant, then the regions of use can be adjusted to individual tables within a dining area, and specified accordingly. A sound level prevailing in the region of use can be acquired by a decibel measuring device that is optionally arranged on the assigned suction means. It is possible to ascertain, by means of an additional movement sensor, whether people are present at the table in the region of use, or whether the noises acquired by the decibel measuring device originate from adjacent tables or from people outside the region of use. In these cases, in each case individually adjusted operation of the suction means assigned to said region of use can be set and specified.

Depending on the type of contamination feared, other sensor means can also be used, in order to allow for automated adjustment of the individual decontamination measures, or the operation of the respective suction means.

According to an advantageous embodiment of the inventive concept, it is provided that, while carrying out decontamination measures, an operation of air supply means is adjusted to the operation of the suction means, and a supply air volume flow supplied by an air supply means is adjusted to an exhaust air flow suctioned by the suction means. A continuous adjustment of the supply air volume flow supplied by the air supply means to the exhaust air flow suctioned by the suction means makes it possible for there to be no excessive pressure difference generated within one region of use, with respect to adjacent regions or with respect to the surroundings. As a result, undesired airstreams over a plurality of regions of use, or undesired air circulation within the room, can be reduced or completely prevented.

In order to make possible a further reduction of a risk of contamination in the room, in addition to the decontamination measures that are carried out continuously, it is optionally provided for disinfection of the room to take place at temporal intervals, using a disinfection means. Thus, disinfection of the room can be carried out using suitable disinfection means, for example in time periods in which only a very small number of people, or no-one, is present in the room. For this purpose, a disinfection agent can be atomized in the room, for example using a cold atomization device, such that the disinfection agent is deposited on all accessible surfaces and decontaminates the surfaces. It can also be provided for all the surfaces or surfaces within regions of use having an increased use intensity to be disinfected at temporal intervals. The intensity of such additional disinfection of the room with disinfection agent, and separate disinfection means, can be adjusted manually or automatically to the actual use of the room. The use of the room can be estimated or determined from the acquired use of the individual regions of use.

The invention also relates to a method for monitoring the decontamination measures mentioned above. In this case it is provided, for at least one property of the air volume contained in the room to be acquired by a monitoring means, for a monitoring signal to be generated if a value outside of a predetermined property range is acquired for the at least one monitored property. The monitoring means can comprise at least one and optionally a plurality of measuring sensors, by means of which a property of the air volume contained in the room, which is relevant for the decontamination measures, can be measured. As long as the measured values of the measuring sensors are located within a range which was specified for the property in question, no change or adjustment of the decontamination measures is required. However, as soon as a measured value is outside of the specified property range, an adjustment of the decontamination measures may be expedient, and may be carried out either by manual intervention or automatically. The monitored properties of the air volume contained in the room may be any properties which may be relevant for the people in the room and for the expected use of the room by said people. Thus, for example the carbon dioxide content of the room air can be monitored.

It is optionally provided for a pressure difference between the air volume monitored by the method and an ambient pressure outside the monitored room to be acquired by the monitoring means. It has been found that, in particular in the case of a long stay of individual people in the room, an excessive pressure difference between the air volume contained in the room and the typical air pressure in the surroundings or outside the monitored room is perceived as uncomfortable, and can even lead to a notable negative impact on the person. It is known that an excessive pressure difference, and in particular a long-lasting negative pressure, in a room can lead to significant harm to the people in said room, up to death. A pressure difference of less than 10 Pa is considered advantageous. For this reason, continuous monitoring of the pressure difference, which is generated by the operation of the suction means, is an important measure associated with carrying out the decontamination measures. The pressure difference can be performed using commercially available pressure difference measuring devices, as are also used for the blower door tests that are known from practice.

According to an advantageous embodiment of the inventive concept it is provided for a contamination content of the air volume monitored by the method to be acquired by the monitoring means. Thus, for example the number of suspended particles can be acquired or estimated, which can be acquired by the monitoring means within a specified time period. This number can be considered a parameter for contamination of the room with the suspended particles in question. The carrying out of the decontamination measures, and in particular the operation of the individual suction means, can then be adjusted according to the monitoring signals of the monitoring means, and accordingly for example according to a contamination content acquired by the monitoring means, such that a higher suction capacity for the suction means is specified in the case of a higher contamination content.

Embodiments of the inventive concept will be explained in greater detail in the following, said embodiments being shown schematically in the drawings.

DETAILED DESCRIPTION

Figure 1:
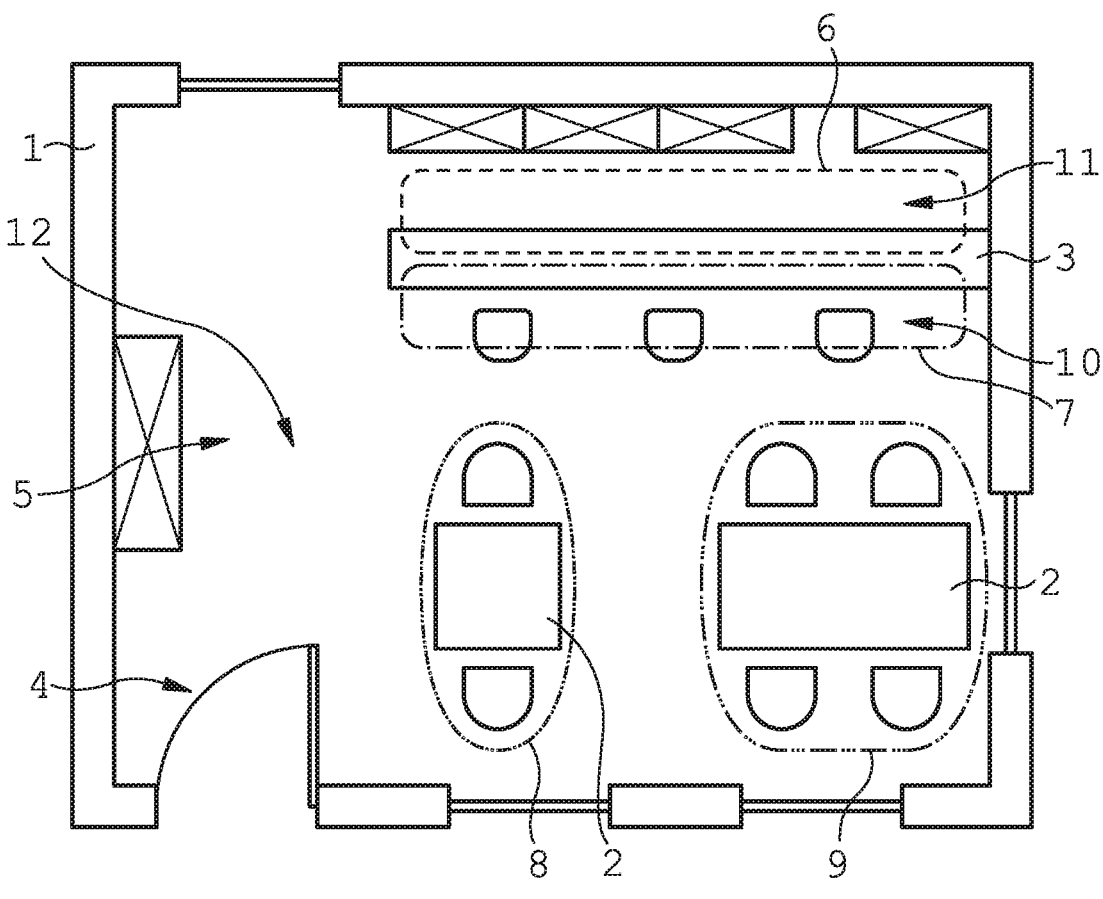
FIG. 1 is a schematic view of a floor plan of a seating area of a restaurant, in which various regions of use are drawn.

FIG. 1 shows a dining room of a restaurant, by way of example for a room 1 located in a building and used by people. In the floor plan of the room 1, shown merely schematically, a plurality of tables 2 for customers, a long bar 3, and entrance region 4 and a cloakroom region 5 are drawn in. In the case of the method for preparing decontamination measures, firstly, in a planning acquisition step, various regions of use 6, 7, 8, 9 within the room 1 are identified, in which regions people spend time more frequently or for a longer period, when the room 1 is used as intended. The regions of use 6, 7, 8, 9 identified in the embodiment by way of example comprise the table 2 as well as bar customer region 10 in front of the bar 3, and a bar service region 11 behind the bar 3. Individual customers can spend time sitting or standing at the bar 3, in the bar customer region 10, and can consume drinks or snacks there. The bar 3 is managed by a waiter, who is typically in the bar service region 11.

The individual regions of use 6, 7, 8, 9 are in each case delimited regions within the room 1. A usable area of the room 1 that is not covered by the regions of use 6, 7, 8, 9 is considered the non-use region 12.

For each region of use 6, 7, 8, 9, in a planning implementation step an expected use intensity, in the case of typical use of the room 1 as intended, by people, is determined. It is thus assumed, for example, that the seats at the tables 2 during operation of the restaurant are substantially continuously used by people, who each spend a long time there, and in this case form a significant contamination risk for other people in the same room 1. These two regions of use 8, 9, which are delimited by a twofold dot-dash line and a threefold dot-dash line are assigned a high use intensity.

The region of use 7 which is associated with the bar customer region 10 and is shown by a single dot-dash line is assigned a medium use intensity. The region of use 6 which corresponds to the bar service region 11 is assigned a low use intensity, since it is provided, in the use concept of this room 1, for the waiting staff to be in the bar service region 11 only when required, and otherwise to be responsible for serving at the tables 2.

Proceeding from the use intensity thus ascertained, a suction means assigned to the relevant region of use 6, 7, 8, 9 is specified for each region of use 6, 7, 8, 9, and a suction volume flow adjusted for the relevant region of use 6, 7, 8, 9, and the expected use intensity is specified. When specifying the suction means and the suction capacity thereof, or a maximum suction volume flow that can be generated by the relevant suction means, information and simulations relating to individual suspended particles are used, which particles can be introduced into the respective region of use 6, 7, 8, 9 by the people, and from there can be contained within the room 1 or can be suspended in the air in an increased concentration compared with the non-use region 12. The suction capacity of the suction means assigned to the individual regions of use 6, 7, 8, 9 is calculated and specified, on the basis of this information, such that the suspended particles contained in the air, in the regions of use 6, 7, 8, 9, can be suctioned with a sufficiently high degree of likelihood, before contamination of another person, also spending time within the region of use 6, 7, 8, 9 in question, by said suspended particles, can occur. In the embodiment shown, the suction capacity of the suction means assigned to the regions of use 8, 9 at the tables 2 is the greatest. The suction capacity of the suction means assigned to the region of use 7 of the bar customer region 10 is less in comparison therewith. The lowest suction capacity is provided for the suction means which is assigned to the region of use 6 of the bar service region 11.

Figure 2:
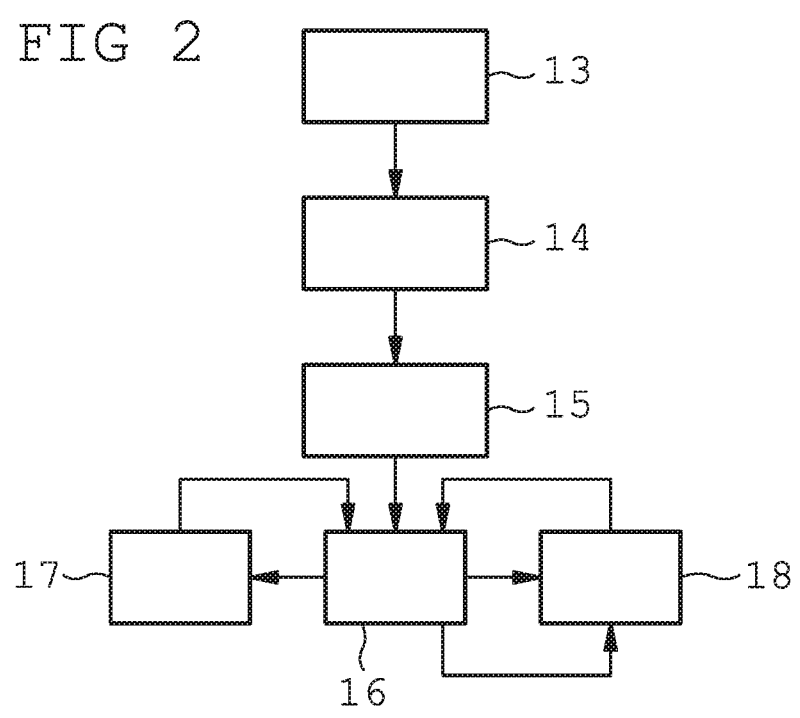
FIG. 2 is a flow diagram for a sequence, by way of example, of the method for preparing, carrying out, and monitoring decontamination measures.

FIG. 2 schematically shows a sequence, by way of example, of the method for decontaminating a room, for example the room 1 in the restaurant. In a planning acquisition step 13, on the basis of a specified use concept, a plurality of regions of use 6, 7, 8, 9 within the room 1 is identified, and for each region of use 6, 7, 8, 9 an expected use intensity is determined on the basis of previously determined parameters. In a subsequent planning implementation step 14, for each region of use 6, 7, 8, 9, proceeding from the expected use intensity, a suction means assigned to said region of use 6, 7, 8, 9 and having an associated supply air volume flow is specified.

As soon as the preparation of the decontamination measures is completed, in a subsequent arrangement step 15 all the required constructional measures can be carried out, in order to subsequently be able to carry out the prepared decontamination measures in the room 1. In this case, the assigned suction means and at least one air supply means for filtered and cleaned fresh air is installed for each region of use 6, 7, 8, 9. Airlock systems are installed at all entrances through which people can enter the room 1. Furthermore, for example hand disinfection or temperature measurement of people entering the room 1 through the airlock system can take place in said airlock systems. The monitoring means required for monitoring the decontamination measures, and a disinfection means possibly required for separate disinfection measures, are installed. In addition, a negative pressure can be generated, and a negative pressure differential measurement can be carried out in order to identify whether the room 1 should be additionally sealed at some points, in order to prevent the penetration of uncleaned air while decontamination measures are being carried out.

During a step 16 of carrying out, the suction means are operated simultaneously with the room 1 being used by people. At the start of the step 16 of carrying out, a monitoring step 17 which is carried out simultaneously and for the duration of the decontamination measures is also initiated. During the monitoring step 17, at least one property of the air volume contained in the room 1 is acquired by a monitoring means, and a monitoring signal is generated if a value outside of a predetermined property range is acquired for the at least one monitored property. The decontamination measures can be adjusted, or suitable additional measures initiated, depending on the acquired and monitored properties.

Irrespective thereof, while the decontamination measures are being carried out, operation of individual suction means can be adjusted to an actual use of the assigned region of use by people, and a suction volume flow suctioned by the suction means in question can be specified, between a minimum value specified for the suction means in question, and a maximum value. For this purpose, a use acquisition step 18 can be carried out at temporal intervals or continuously, and a parameter for an actual use of the regions of use 6, 7, 8, 9 in the room 1 can be determined by a suitable sensor means. Depending on the determined parameters, in each case the suction means in question can then be adjusted, and optionally operated more or less intensively.

Figure 3:
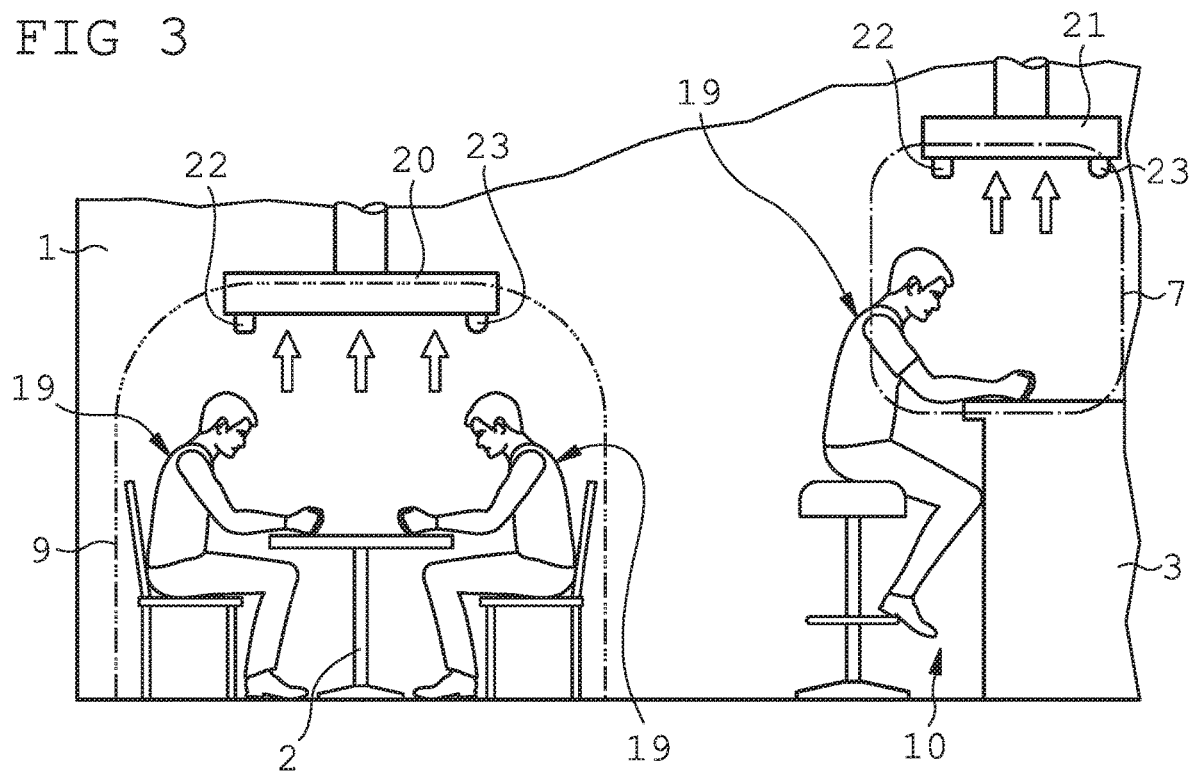
FIG. 3 is a schematic partial view of the seating area shown in FIG. 1, while the decontamination measures are being carried out.

FIG. 3 shows a view of a part of the room 1 during use by several people 19. Two people 19 are sitting at the table 2, in the region of use 9. One person 19 is sitting at the bar 3 in the bar customer region 10.

A suction means 20 is arranged above the table 2. A further suction means 21 is arranged above the bar customer region 10. The spacing of the suction means 20, 21 from the heads of the people 19 is adjusted to the use of the relevant region of use 9, 10, to be expected in each case, by the people 19. As a result, a targeted airflow can be promoted, and the capture region of the suction means 20, 21 can be specified such that, during use as intended, the heads of the people 19 are largely in said capture region.

Both suction means 20, 21 are in each case equipped with a decibel measuring sensor 22 and with a movement sensor 23. If no movement is determined by the movement sensor 23 over a long period of time, the capacity of the assigned suction means 20, 21 can be reduced or said means can be deactivated. In addition, an adjustment of the suction capacity of the suction means 20, 21 can be carried out via a measurement of the noise level by means of the decibel measuring sensor 22.

Figure 4:
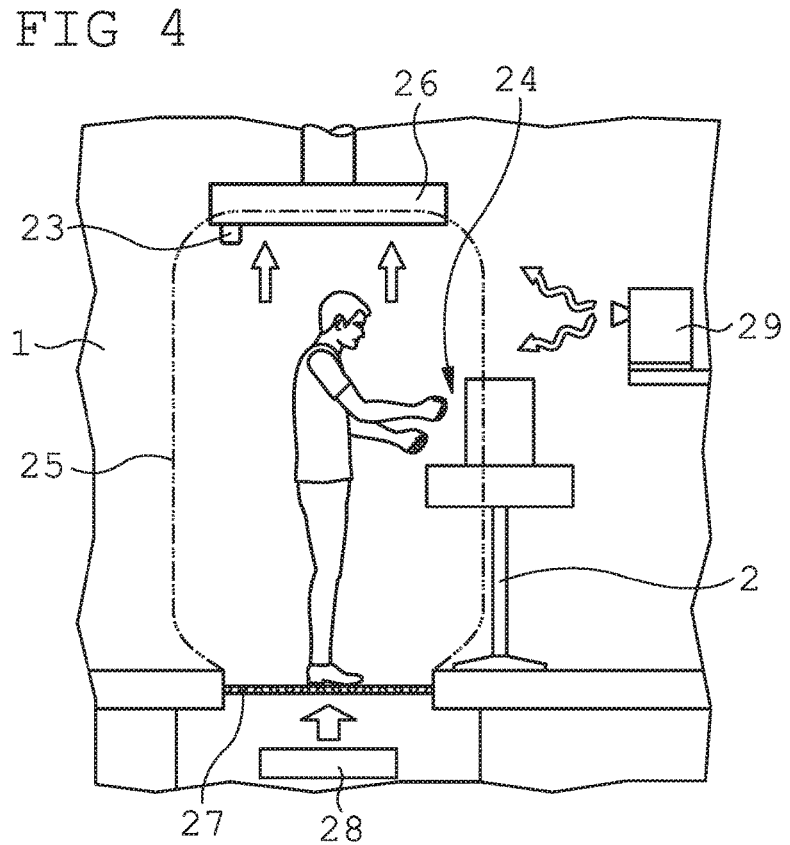
FIG. 4 is a view of a workstation in a manufacturing plant, while the decontamination measures are being carried out.

FIG. 4 shows, by way of example, a workstation 24 in a production company, which workstation forms a region of use 25 that is indicated by a fourfold dot-dash line. In addition to a suction means 26, an air-permeable grating 27 is arranged under the workstation 24, and an air supply means 28 under said grating. Filtered and cleaned fresh air is supplied by the air supply means 28. Optionally, contaminated air is suctioned out of the region of use 25 by the suction means 26. The suction means 26 comprises merely one movement sensor 23, since the noise level typically prevailing in the production company is superimposed with the noises of the person 19 at the workstation 24, and an actuation of the suction means 26 that is adjusted to the sound level in the workstation 24 is expedient.

A targeted airflow can be promoted by the arrangement of the air supply means 28 under the region of use 25 and the suction means 26 above the region of use 25. The delivery rate of the air supply means 28 is adjusted to the suction capacity of the suction means 26, such that an airflow course extending from the air supply means 28 to the suction means 26 is achieved, and thus a targeted airflow is brought about in the region of use 25, even without additional structural measures.

In the production company, a disinfection means 29 is arranged beside the workstation 24, which disinfection means comprises a cold atomization device by means of which the workstation 24 and all the surfaces located there are disinfected at time intervals, for example every night, using an atomized disinfection agent.

Figure 5:
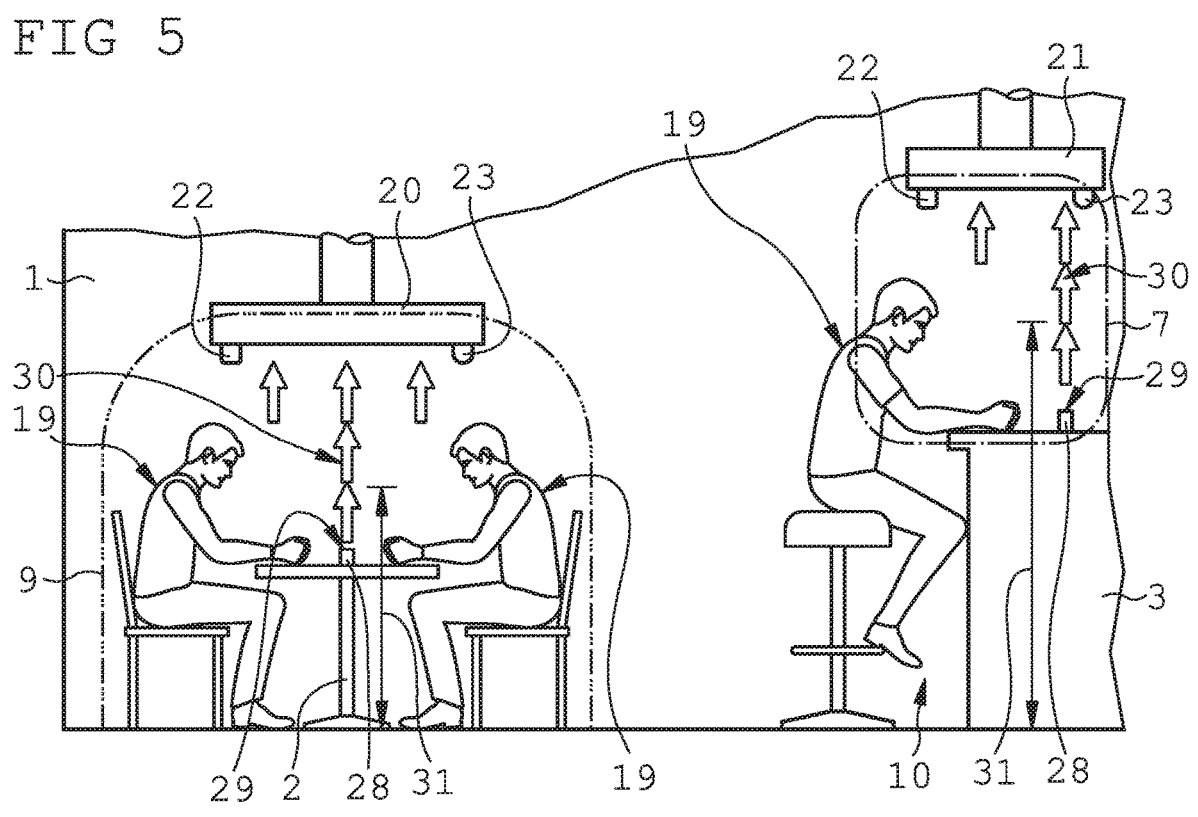
FIG. 5 shows the seating area according to FIG. 3, wherein an air curtain is provided in each of the regions of use, in order to reduce a propagation of breathable air from people.

FIG. 5 shows a further view of the room 1 shown in FIG. 3. A strip-shaped outlet opening 29 of the air supply means 28 (indicated only schematically) is arranged on an upper surface of the table 2 in the region of use 9. The strip-shaped outlet opening 29 is arranged in the middle of the table 2, between the two seats on opposite sides of the table 2, and extends substantially over the length of the table 2. The filtered and cleaned fresh air flowing out through the strip-shaped outlet opening 29 is suctioned in by the suction means 20 which is arranged above the table 2. In this way, an air curtain having a very predominantly laminar suction flow 30 is formed by the strip-shaped outlet opening 29 of the air supply means 28 on the surface of the table 2 as far as the suction means 20. The suction flow 30 extends in particular beyond the breathable air altitude 31 in the vertical direction, at which altitude people 19 breathe out the highest breath volume during use of the region of use 9 as intended. In the example shown, this is the average head height of the people 19 seated at the table 2. The air curtain formed by the suction flow 30 divides the region of use 9 into two use cells which substantially correspond to the two seats. Each person 19 spends a long time in the use cell assigned to said person 19. An air exchange between the two use cells is reduced by the air curtain. Furthermore, the aerosols breathed out by the people 19, which aerosols may contain viruses or bacteria, are captured and carried along by the suction flow 30, in particular from the environment of the breathable air altitude 31, such that the aerosols are suctioned particularly effectively by the suction means 20 and cannot spread into the surroundings.

A strip-shaped outlet opening 29 of the air supply means 28 (not shown in greater detail) is also arranged on the bar 3, in the region of use 7. The strip-shaped outlet opening 29 extends over the entire length of the bar 3. Fresh air is supplied to the region of use 7 via the strip-shaped outlet opening 29, which fresh air is suctioned by the suction means 21 above the bar 3. As a result, in this region of use 7, too, an air curtain is formed, consisting of a suction flow 30 that flows upwards in a substantially laminar manner, and which shields the person 19 sitting in front of the bar 3 from a person standing behind the bar 3. In this case, the breathable air altitude 31 is specified so as to be higher than in the region of use 9, on account of the deviating sitting position and posture of the person 19.

Figure 6:
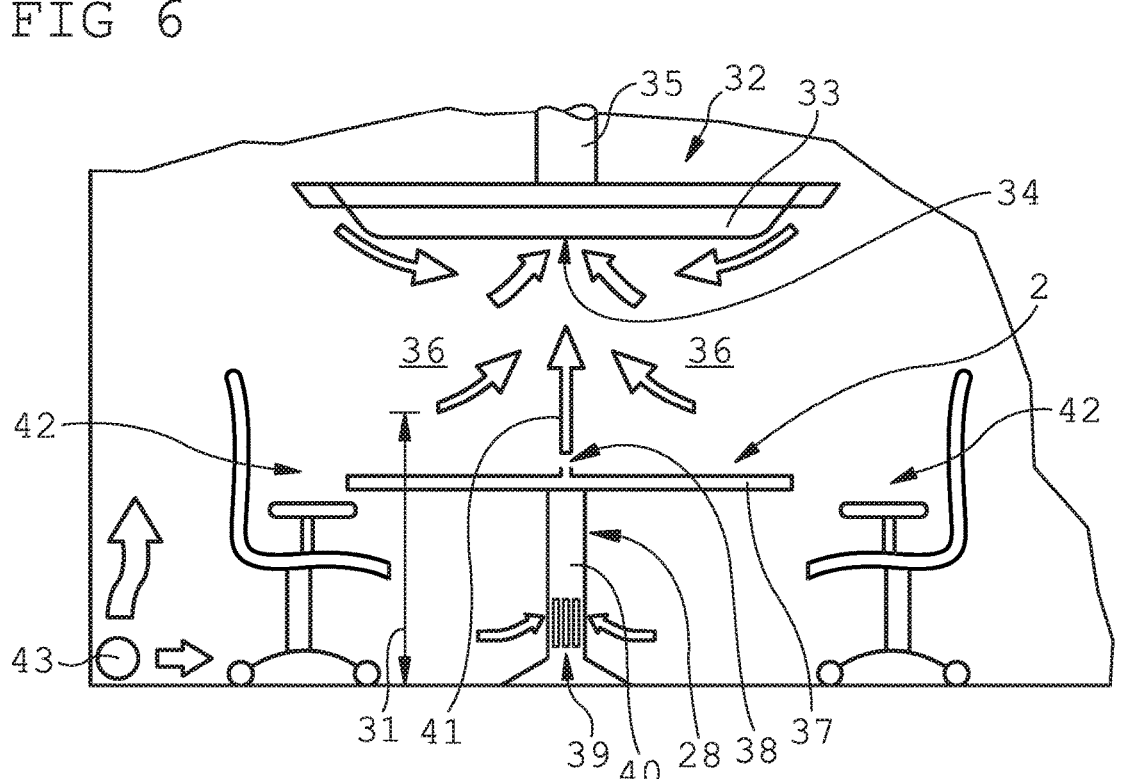
FIG. 6 is a side view of a device for carrying out the decontamination measures in an office space.
Figure 7:
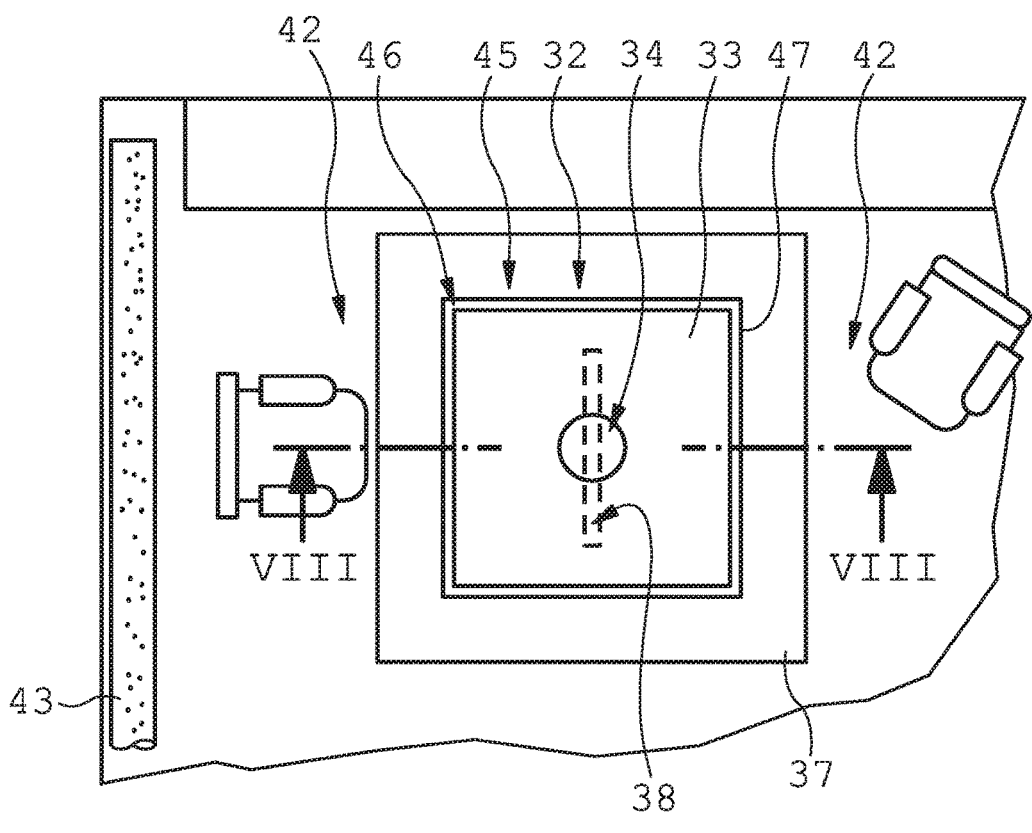
FIG. 7 is a plan view of the office space shown in FIG. 6.
Figure 8:
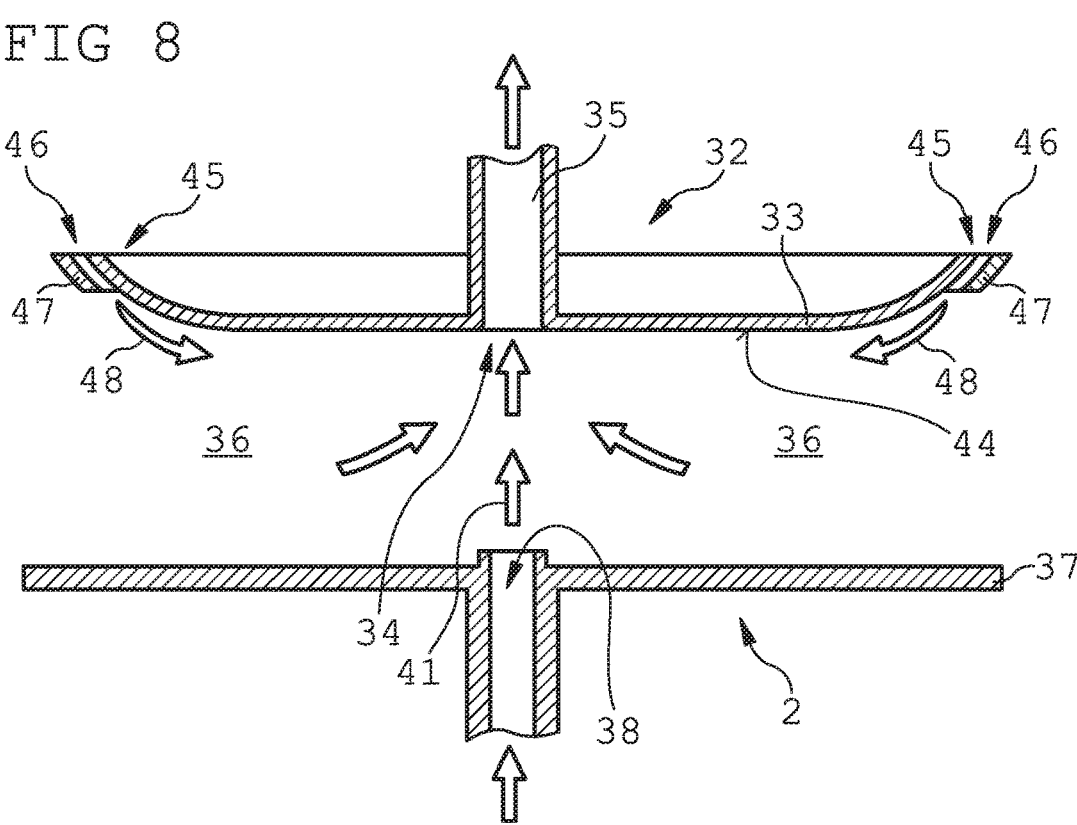
FIG. 8 is a sectional view along a line VIII-VIII in FIG. 7, through a part of the device.

FIGS. 6 to 8 show, by way of example, a deviating embodiment of a device for carrying out decontamination measures. In this case, a desk used by two people is shown by way of example for a typical region of use 7 in an office space. The device comprises a suction means 32 comprising a flow guidance plate 33, in the center of which a circular suction opening 34 having a diameter of between approximately 12 cm and 18 cm is arranged. Room air can be suctioned through the suction opening 34 from a capture region 36 located therebelow, via a suction channel 35.

The suction means 32 is arranged above a tabletop 37 of a table 2. An air supply means 28 having a strip-shaped air supply nozzle 38 is arranged in the tabletop 37. By means of air supply nozzle suction openings 39 in the table legs 40 of the table 2, room air can be suctioned from under the tabletop 37 and blown through the air supply nozzle 38, in the direction of the suction means 32, as a strip-shaped supply airstream 41. This results in a strip-shaped flow wedge, which extends in the direction of the suction means 32 with an initially predominantly laminar flow, and separates two use cells 42, on the two opposite sides of the tabletop 37, from one another.

A diffuser tube 43 having a diameter of between approximately 5 cm and 15 cm, and a perforated metal plate-like lateral surface is located in a room corner. Fresh air is supplied to the room and also the use cells 42 via the diffuser tube 43.

The dimensions of the flow guidance plate 33 shown schematically in the plan view according to FIG. 7 are slightly smaller than the dimensions of the tabletop 37 above which the suction means 32 is arranged at a height of approximately 80 cm to 100 cm above the tabletop 37.

The flow guidance plate 33 comprises a convexly curved flow guidance surface 44 in the direction of the tabletop 37. The flow guidance surface 44 can also be designed planar. A suction gap 46 is formed on a side facing the air supply nozzle 38, along a peripheral edge 45 of the flow guidance plate 33, which gap is delimited by a gap strip 47 which is arranged on the peripheral edge 45, at a spacing of from approximately 1 cm to 2 cm, in parallel with the flow guidance surface 44. The room air suctioned in the capture region 36 is suctioned back through the suction gap 46, wherein a Coandă effect is generated by the suction gap 46 and the exhaust air flow 48 suctioned through the suction gap 46 is guided along the flow guidance surface 44, in the direction of the suction opening 34, over a comparatively large distance, and detaches from the flow guidance surface 44 only very late, if at all. As a result, very efficient capture and suctioning of the room air from a large capture region 36 is promoted.

Figure 9:
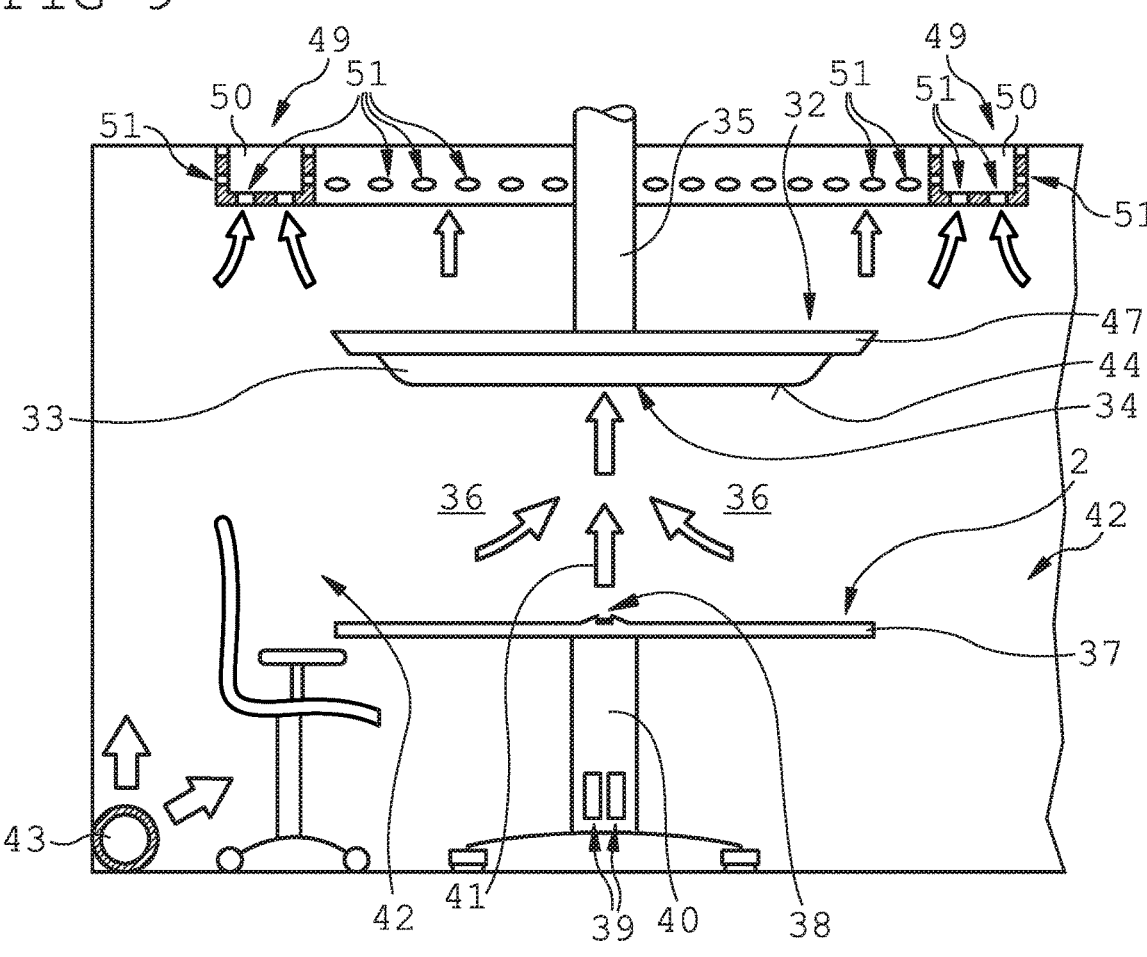
FIG. 9 is a schematic view of a device in an office space, wherein an additional room air suction means is also shown, in a partially cutaway view.

FIG. 9 shows, in addition to the device shown in FIGS. 6 to 8, a room air suction means 49 which supplements the device. The room air suction means 49 comprises an annularly shaped room air suction channel 50 which surrounds the suction means 32 together with the flow guidance plate 33 and the suction opening 34 formed therein. A number of room air suction openings 51 are formed in the room air suction channel 50, through which openings room air can be suctioned. The room air suction openings 51 take up approximately 20% to 50% of an outer surface of the room air suction channel 50 facing the room. In the case of an embodiment of the room air suction channel 50 which is considered particularly advantageous, the room air suction openings 51 occupy a surface area of approximately 30% of the outer surface of the room air suction channel 50 facing the room, wherein the room air can be suctioned through said room air suction openings 51 at a flow speed of approximately 0.3 m/s.

Figure 10:
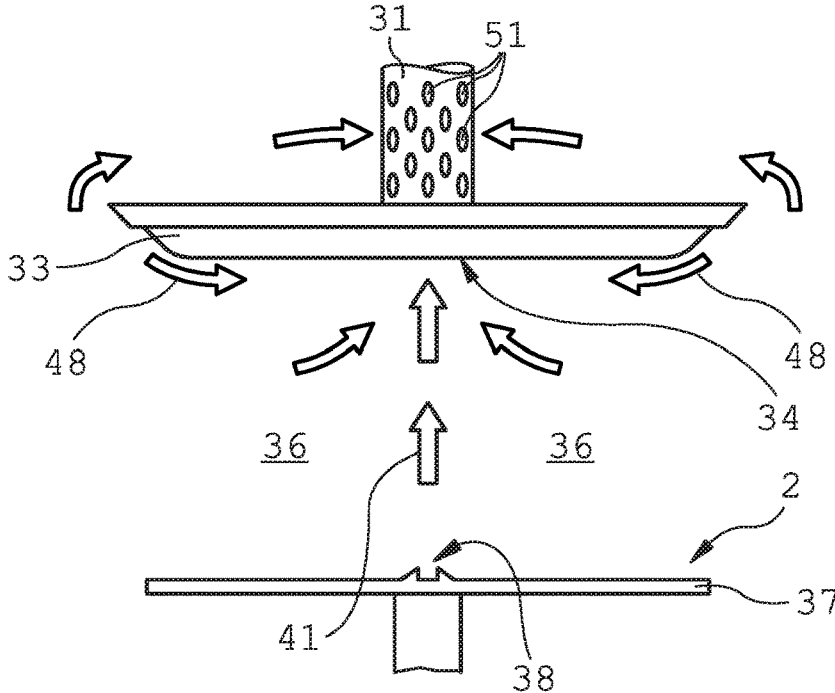
FIG. 10 is a schematic side view through a part of the device as in FIG. 8.

In an embodiment of the device shown schematically in FIG. 10, the room air suction device 49 (not otherwise shown) comprises a plurality of room air suction openings 51 which are arranged in the suction channel 35 through which the room air, suctioned through the suction opening 34, is suctioned out of the capture region 36. Room air is suctioned in particular out of a region directly above the flow guidance plate 33, through the room air suction openings 51 formed in the suction channel 35. In this way, aerosols, a very small quantity of which could flow laterally around the flow guidance plate 33 and collect above the flow guidance plate 33, can be efficiently suctioned. The suction channel 35 can optionally be formed by guide plates or beads, arranged in the interior thereof, around the room air suction openings 51, such that the room air suctioned through the suction opening 34 cannot escape again through the room air suction openings 51.

Figure 11:
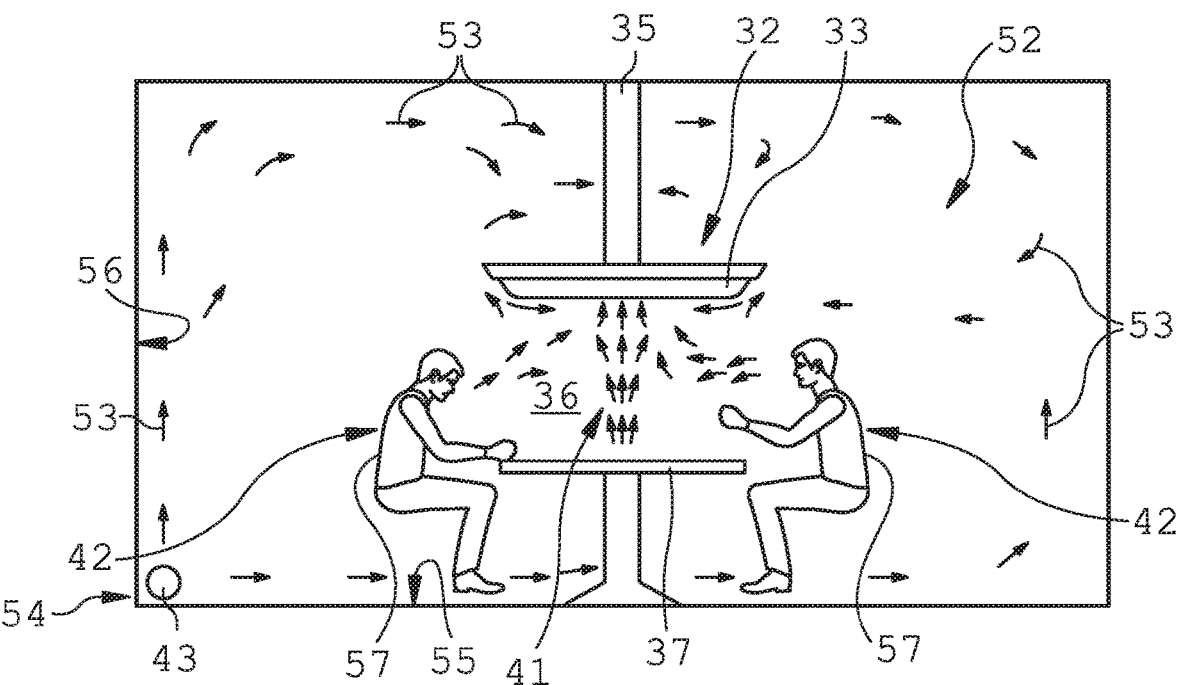
FIG. 11 is a schematic view of an airflow forming in an office space during operation of the device.

FIG. 11 schematically shows the results of a simulation of operation of the device within an office space 52. In this case, the arrows 53 within the office space 52 symbolize the course and the intensity of room airflows occurring within the office space 52. Fresh air is blow into the office space via the diffuser tube 43 extending along a room edge 54, on a room floor 55. In this case, airstreams preferably form in a rising manner along a room wall 56, and in a horizontally extending manner along the room floor 55. The supply airstream 41 generated between the tabletop 37 and the suction opening 34 in the flow guidance plate 33 results in a strip-shaped flow wedge, which extends in the direction of the suction opening 34 of the suction means 32 with an initially predominantly laminar flow, and prevents room air spreading from one use cell 42 into the opposite use cell 42. In particular, the strip-shaped supply airstream 41 prevents air breathed out by a person 57 within a use cell 42 being able to flow into the opposite use cell 42.

Figure 12:
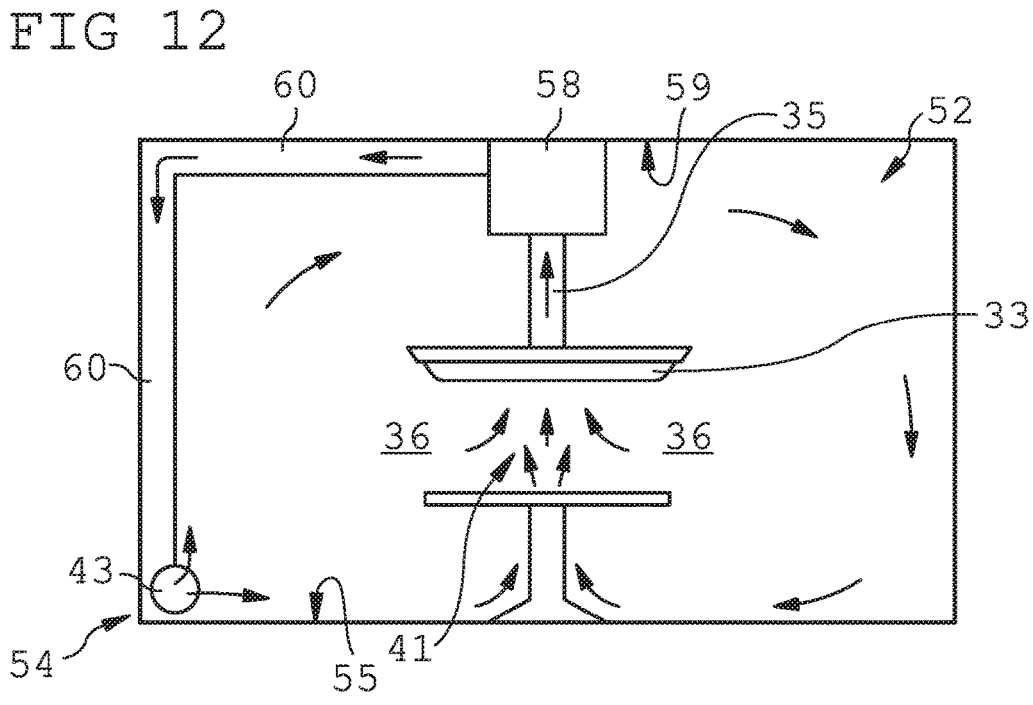
FIG. 12 is a schematic view of an office space comprising a diffuser tube, for the supply of fresh air, arranged along a room edge in a transition region between a room floor and a room wall.
Figure 13:
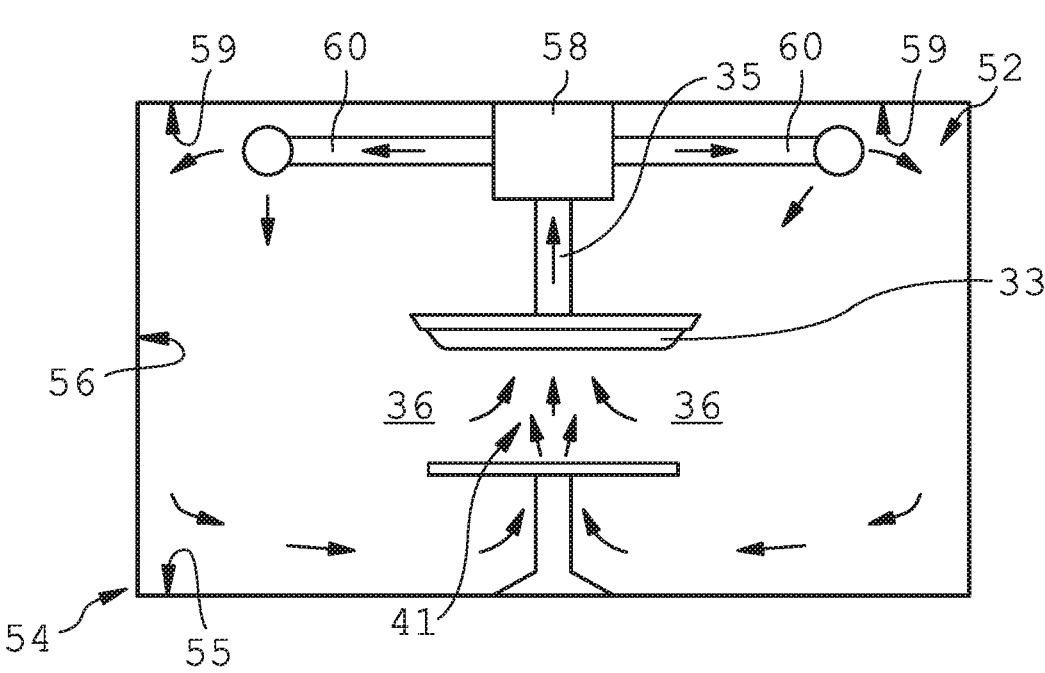
FIG. 13 is a schematic view according to FIG. 12, wherein a plurality of diffuser tubes is arranged under a room ceiling.
Figure 14:
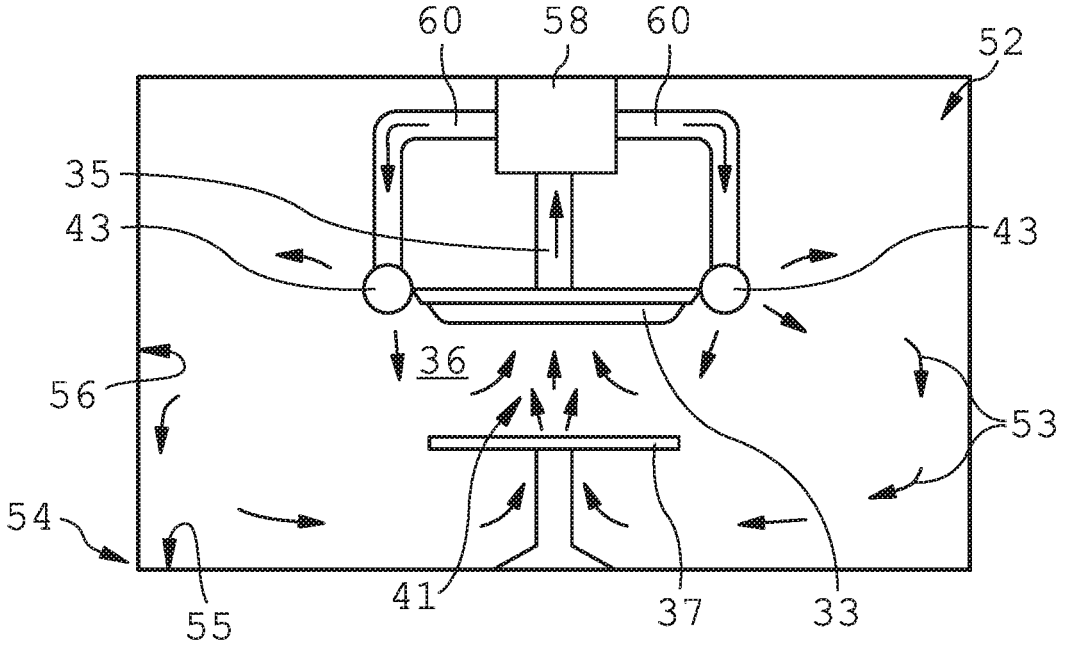
FIG. 14 is a schematic view according to FIGS. 12 and 13, wherein a diffuser tube is arranged adjacently to the flow guidance plate.

FIGS. 12 to 14 schematically show, by way of example, different variants of the flow guide within the office space 52. In all the embodiments shown, the room air is merely circulated. The supply airstream 41 blown out by the air supply nozzle 38 is suctioned together with further room air from the capture region 36 of the flow guidance plate 33, through the suction opening 34 into the suction channel 35 and supplied to a cleaning device 58 which is arranged above the flow guidance plate 33, on a room ceiling 59. Here, the supply airstream 41 suctioned out is cleaned using suitable filter means and optionally additional air treatment means, such as UV light sources or plasma cleaning devices, and impurities contained in the suctioned-out supply airstream 41 are filtered out. In particular HEPA filters of filter class H 13/14 are suitable for this purpose. Subsequently, the cleaned exhaust air is supplied to the respective diffuser tubes 43 as fresh air, via fresh air channels 60.

The embodiment shown in FIG. 12 substantially corresponds to the variant also shown in FIGS. 9 and 11. The fresh air is supplied to the office space 52 again to the office space 52, via a diffuser tube 43 extending along the room edge 54, on the room floor 55. Room airstreams extending around the use cells 42 are advantageously formed.

In the embodiment shown in FIG. 13, two or more diffuser tubes 43 are arranged below the room ceiling 59 but above the flow guidance plate 33.

In the embodiment shown in FIG. 14, an annularly formed diffuser tube 43 laterally surrounds the flow guidance plate 33.

The invention claimed is:

1. A device for carrying out decontamination measures within a room (1) located in a building and used by people (19), comprising:
a suction means (20, 21, 32) that is assigned to a region of use (7, 9), the region of use (7, 9) having at least two use cells (42) within the region of use (7, 9); and
an air supply means (28),
wherein the suction means (20, 21, 32) comprises a suction opening (34) which is arranged in a flow guidance plate (33) which surrounds the suction opening (34) and is arranged above a specifiable breathable air altitude (31),
wherein the air supply means (28) comprises a strip-shaped air supply nozzle (38) which is arranged between the at least two use cells (42) and under the suction opening (34),
wherein the nozzle generates a strip-shaped supply airstream (41) such that, when the device is operated as intended, an initially strip-shaped supply airstream (41) is converted into a suction flow (30) which conveys air out of the breathable air altitude (31) to the suction means (20) and suctions it through the suction opening (34), wherein the flow guidance plate (33) comprises, at least in portions, a suction gap (46) along a peripheral edge (45) thereof, on a side thereof directed towards the air supply means (28),
wherein an exhaust air flow flows along a flow guidance surface (44) of the flow guidance plate (33) in the direction of the suction opening (34), and
wherein the suction gap generates a Coanda effect, thereby guiding the exhaust air flow along on the flow guidance surface (44).

2. The device according to claim 1,
wherein the flow guidance plate (33) comprises a convex or planar flow guidance surface (44) facing away from the air supply means (28).

3. The device according to claim 1, further comprising a room air suction means (49) which comprises room air suction openings (51) above the flow guidance plate (33).

4. The device according to claim 3,
wherein the room air suction means (49) comprises at least one room air suction opening (51) in a suction channel (35) that leads into the suction opening (34).

5. A device for carrying out decontamination measures within a room (1) located in a building and used by people (19), comprising:
a suction means (20, 21, 32) that is assigned to a region of use (7, 9), the region of use (7, 9) having at least two use cells (42) within the region of use (7, 9); and
an air supply means (28),
wherein the suction means (20, 21, 32) comprises a suction opening (34) which is arranged in a flow guidance plate (33) which surrounds the suction opening (34) and is arranged above a specifiable breathable air altitude (31),
wherein the air supply means (28) comprises a strip-shaped air supply nozzle (38) which is arranged between the at least two use cells (42) and under the suction opening (34),
wherein the nozzle generates a strip-shaped supply airstream (41) such that, when the device is operated as intended, an initially strip-shaped supply airstream (41) is converted into a suction flow (30) which conveys air out of the breathable air altitude (31) to the suction means (20) and suctions it through the suction opening (34), and
wherein the device comprises at least one diffuser tube (43) which comprises a plurality of diffuser openings that are spaced apart in an axial direction and are oriented differently in peripheral directions, through which openings fresh air can be supplied to the region of use.

6. The device according to claim 5,
wherein the flow guidance plate (33) comprises, at least in portions, a suction gap (46) along a peripheral edge (45) thereof, on a side thereof directed towards the air supply means (28),
wherein an exhaust air flow flows along a flow guidance surface (44) of the flow guidance plate (33) in the direction of the suction opening (34), and
wherein the suction gap generates a Coandă effect, thereby guiding the exhaust air flow along on the flow guidance surface (44).

7. The device according to claim 5,
wherein the diffuser tube (43) is arranged at a distance from the air supply means (28) and the suction means (32), along a room edge (54) of the room (1).

8. The device according to claim 5, wherein the at least one diffuser tube (43) is arranged laterally beside the flow guidance plate (33) or above the flow guidance plate (33).

9. A device for carrying out decontamination measures within a room (1) located in a building and used by people (19), comprising:

a suction means (20, 21, 32) that is assigned to a region of use (7, 9), the region of use (7, 9) having at least two use cells (42) within the region of use (7, 9); and an air supply means (28), wherein the suction means (20, 21, 32) comprises a suction opening (34) which is arranged in a flow guidance plate (33) which surrounds the suction opening (34) and is arranged above a specifiable breathable air altitude (31), wherein the air supply means (28) comprises a strip-shaped air supply nozzle (38) which is arranged between the at least two use cells (42) and under the suction opening (34), wherein the nozzle generates a strip-shaped supply air-stream (41) such that, when the device is operated as intended, an initially strip-shaped supply airstream (41) is converted into a suction flow (30) which conveys air out of the breathable air altitude (31) to the suction means (20) and suctions it through the suction opening (34), wherein the device further comprises a room air suction means (49) which comprises room air suction openings (51) above the flow guidance plate (33), and wherein the room air suction means (49) comprises a room air suction channel (50) which comprises a number of room air suction openings (51) and which annularly surrounds the suction opening (34), at a distance from the suction opening (34).

\* \* \* \* \*